(12) United States Patent
Hudson et al.

(10) Patent No.: US 6,656,473 B2
(45) Date of Patent: *Dec. 2, 2003

(54) TRYPTOPHAN SOURCE FROM PLANTS AND USES THEREOF

(76) Inventors: Susan P. Hudson, 253 Cambria Street, Stratford, Ontario (CA), N5A 1H9; Craig J. Hudson, 253 Cambria Street, Stratford, Ontario (CA), N5A 1H9

(*) Notice: Subject to any disclaimer, the term of this patent is extended or adjusted under 35 U.S.C. 154(b) by 155 days.

This patent is subject to a terminal disclaimer.

(21) Appl. No.: 09/902,096

(22) Filed: Jul. 11, 2001

(65) Prior Publication Data

US 2002/0004049 A1 Jan. 10, 2002

Related U.S. Application Data

(63) Continuation-in-part of application No. 09/580,914, filed on May 26, 2000, now Pat. No. 6,503,543.

(51) Int. Cl.$^7$ .......................... A61K 35/78; A01N 43/38
(52) U.S. Cl. .................. 424/195.17; 424/725; 424/750; 424/757; 424/758; 424/768; 424/776; 514/419; 514/909; 514/910; 514/923
(58) Field of Search ............................ 424/725, 195.17, 424/750, 757, 758, 768, 776, 439; 435/108; 514/923, 909, 910, 419

(56) References Cited

U.S. PATENT DOCUMENTS

| | | | |
|---|---|---|---|
| 2,638,433 A | | 5/1953 | George |
| 3,930,055 A | | 12/1975 | Engelman |
| 4,054,665 A | * | 10/1977 | Eberle et al. |
| 4,307,118 A | | 12/1981 | Kajs |
| 4,421,746 A | | 12/1983 | Kojima et al. |
| 4,551,335 A | * | 11/1985 | Canella et al. |
| 4,687,763 A | * | 8/1987 | Wurtman |
| 4,897,380 A | | 1/1990 | Pollack et al. |
| 5,002,780 A | | 3/1991 | Bakta et al. |
| 5,277,910 A | | 1/1994 | Hidvegi |
| 5,470,846 A | | 11/1995 | Sandyk |
| 5,567,424 A | | 10/1996 | Hastings |
| 5,612,074 A | | 3/1997 | Leach |
| 5,738,887 A | | 4/1998 | Wu |
| 5,882,672 A | | 3/1999 | Kojima et al. |
| 5,885,976 A | | 3/1999 | Sandyk |
| 5,919,511 A | | 7/1999 | Hagiwara |
| 5,968,519 A | | 10/1999 | Youssefyeh et al. |
| 6,245,364 B1 | * | 6/2001 | Jones et al. |
| 6,294,520 B1 | | 9/2001 | Naito |

FOREIGN PATENT DOCUMENTS

| | | |
|---|---|---|
| EP | 0 147 688 | 7/1985 |
| EP | 0 652 012 A1 | 5/1995 |
| FR | 1.485.766 | 6/1967 |
| FR | 2 777 751 | 10/1999 |
| GB | 388319 | 2/1933 |
| WO | WO 95/19716 | 11/1995 |
| WO | WO 99/61038 | 5/1999 |

OTHER PUBLICATIONS

Betz et al, *Science*, 202:225–227 (1978).
Boman, *Aust. NZ J. Psychiatry*, 22:83–97 (1988).
Balestrieri et al, *European Journal of Biochemistry*, 90:433–440 (1978).
Fears et al, *British Journal of Nutrition*, 43:349–356 (1980).
Fernstrom et al, *Science*, 174:1023–1025 (1971).
George et al, *Sleep*, 12:345–53 (1989).
Griffiths et al, *Psychobiology*, 9:345–354 (1972).
Hartmann, *American Journal of Psychiatry*, 134:366–370 (1977).
Kotake et al, *American Journal of Nutrition American Journal of Clinical Nutrition*, 24:826–829 (1971).
Lajtha, *Aromatic Amino Acids in the Brain*, (CIBA Foundation Symposium 22) New York: American Elsevier, pp. 25–49 (1974).
Moller, *Human Neurobiology*, 2:41–8 (1983).
Sourkes, *Advances in Biological Psychiatry*, 10:160–173 (1983).
Schneider–Helmet et al, *Psychopharmacology*, 89:1–7 (1986).
Saunders et al, *Clinical and Experimental Pharmacology and Physiology*, 26:11–19 (1999).
Thomas et al, *American Journal of Psychiatry*, 141:281–283 (1977).
Wyatt et al, *Lancet II*, 84:842–846 (1970).
Fernstrom et al, *Science*, 178:414–6 (1972).
Fernstrom et al, *Journal of Nutrition*, 115:1337–44 (1985).
Hartmann, *Journal of Psychiatric Research*, 17:107–13 (1982).
Hartmann et al, *Journal of Nervous and Mental Disease*, 167:497–9 (1979).
Landry et al, *Advances in Experimental Medicine and Biology*, 398:703–9 (1996).
Leathwood et al, *Journal of Neural Transmission—General Section*, 79(1–2):25–34 (1990).
Morin, Appendix F: Sleep diary. In: Insomnia, psychological assessment and management, Guilford Press, New York, pp. 209–211 (1993a).
Morin, Appendix B: Sleep impairment index. In: Insomnia, psychological assessment and management, Guilford Press, New York, pp. 199–200 (1993b).
Allegri et al, Food Chemistry, Vol 47, No. 1, pp. 23–27 (1993).
Oyenuga et al, *J. Sci. Fd Agric.*, 26:843–854 (1975).
Edwards et al, *The Journal of Nutrition*, 32(6):597–611 (1946).

* cited by examiner

Primary Examiner—Christopher R. Tate
Assistant Examiner—Michele Flood
(74) Attorney, Agent, or Firm—Morgan, Lewis & Bockius LLP

(57) ABSTRACT

Compositions are described comprising at least partially defatted meal from a plant source containing protein-bound tryptophan, preferably squash seeds, and, optionally, a carbohydrate source provided in an amount capable of facilitating transport of in vivo generated tryptophan across the blood brain barrier. Also described are dietary supplements, foods and beverages comprising the composition of the invention to induce sleep or provide tryptophan supplementation to individuals in need thereof.

14 Claims, 2 Drawing Sheets

TRYPTOPHAN SOURCE FROM PLANTS AND USES THEREOF

RELATED APPLICATION

This application is a continuation-in-part application of Ser. No. 09/580,914, filed May 26, 2000, now U.S. Pat. No. 6,503,543.

FIELD OF THE INVENTION

This invention relates to compositions comprising natural sources of tryptophan, particularly protein-bound tryptophan from plants, processes for making said compositions; physical formulations of said compositions, and use of said compositions as dietary supplements, food, beverage, and as pharmaceutical compositions for inducing sleep, improving tryptophan metabolism, alleviating reduced levels of serotonin in a human, anxiety disorder, depression, obsessive compulsive, aggression, chronic paid and eating disorder.

BACKGROUND TO THE INVENTION

Tryptophan is an essential amino acid found in numerous naturally occurring plant proteins and which has a number of interesting medicinal qualities including treatment of insomnia as well as an adjunct in the treatment of a number of psychiatric disorders. After absorption, tryptophan circulates in the blood as approximately 80% bound to plasma albumin with the remaining 20% circulating as free tryptophan, and under appropriate conditions, tryptophan is transported into the brain. Once across the blood brain (BBB), tryptophan becomes available for metabolism into serotonin, a neurotransmitter implicated in mood and sleep regulation (Boman, 1988). Serotonin, in turn, is metabolized to melatonin; a sleep related hormone found in the pineal gland, a small cone-like structure in the epithalamus of the brain that regulates the 24-hour circadian rhythm in humans. Ingestion of a sufficient quantity of tryptophan per se consistently results in reduced sleep latency i.e. the time from "lights out" to sleep, and an improvement in overall quality of sleep through improved sleep architecture (Boman, 1988). Tryptophan metabolism to serotonin also serves well in conditions where depleted serotonin levels exists such as anxiety disorders, depression, obsessive-compulsive some pain disorders, aggression and eating disorders.

The hypnotic effects of tryptophan are well studied and follow a fairly flat dose-response curve with a plateau at approximately 1000 mg (for review see Schneider-Helmut and Spinweber, 1986). When given alone, as little as 250 mg of tryptophan is sufficient to produce improved sleep in people with mild insomnia, or in those reporting longer-than-average sleep latency (Hartmann and Spinweber, 1976; Hartmann 1982). Dosages of 1000 mg are associated with more consistent results (Schneider-Helmut and Spinweber, 1986) but higher dosages (2,000–12,000 mg) offer little extra benefit and, indeed, the highest dosages (12,000 mg) are associated with disrupted sleep architecture despite a reduction in sleep latency (Griffiths et al 1972).

There remains a need, however, for addressing the aforesaid medical conditions without administration of "free" tryptophan per se.

SUMMARY OF THE INVENTION

It is an object of the present invention to provide an alternative source of tryptophan for in vivo medical treatment of humans.

It is a further object to provide said alternative source in user friendly forms.

It is a further object to provide an improved method of producing said alternative source.

Thus, in its broadest concept, the invention provides an efficacious and beneficial supply of tryptophan across the blood brain barrier by providing a supply of protein-bound tryptophan from a suitable plant source in an edible, digestible form to generate tryptophan in vivo.

Accordingly, in one aspect the invention provides a composition comprising at least partially defatted meal from a plant source containing protein-bound tryptophan, and a physiologically acceptable diluent or carrier therefor.

A naturally derived, tryptophan-rich composition with several unique characteristics has been developed by enriching the protein-bound tryptophan content of a tryptophan-rich protein source. Compositions of the invention comprise a plant source naturally containing protein-bound tryptophan, preferably squash seeds, such as butternut squash seeds, peppercorn squash seeds and pumpkin seeds. Preferably, the plant source is at least partially defatted to concentrate the protein-bound tryptophan content. The composition further, preferably, comprises a carbohydrate source, such as glucose, in an amount sufficient to enhance uptake of tryptophan across the blood brain barrier and to circumvent the competition for BBB transport sites into the central nervous system (CNS). The composition can further optionally comprise physiologically acceptable vehicle(s), flavorings, colors and other nutrients, such as vitamins, preferably vitamin B3 and/or vitamin B6.

In a preferred embodiment, the composition comprises at least partially defatted squash seeds, particularly butternut squash, pumpkin and peppercorn squash seeds, glucose and vitamins B3 and B6.

The invention further pertains to dietary supplements, in the form of, e.g. a tablet, powder, suspension, liquid, capsule or gel; foods, e.g., dietary bar, cookie, baked good, snack food, candy, candy bars, beverages and like edible foods comprising the composition of the invention.

The compositions of the invention can be used to induce sleep in an individual in need thereof, such as those suffering from insomnia or condition associated with a sleep disorder. Alternatively, the compositions can be administered to an individual to improve their tryptophan metabolism, such as for those individuals suffering from a condition or disease associated with reduced levels of serotonin. The compositions can be used as a hypnotic, but may also serve a role in clinical states associated with reduced levels of serotonin, a tryptophan metabolite: depression, anxiety states including obsessive-compulsive disorder, eating disorders and chronic pain.

Thus, we have discovered, using second derivative spectroscopy, that certain plant sources and, specifically, plant seeds possess relatively high levels of protein-bound tryptophan and that these materials can be used to provide tryptophan in vivo. Accordingly, a process has been developed to produce edible compositions having enhanced levels of protein-bound tryptophan as a natural protein source of tryptophan richer than the known natural source. Plants that use gramine typically contain high levels of tryptophan and can be used herein as the plant source. It is desirable, but not essential, that the starting plant material contain at least 200 mg/100 g or at least 0.2% tryptophan in its protein-bound form. Tryptophan concentration can be determined using known methods, including, for example, high pressure liquid chromatography (HPLC), second derivative spectroscopy or any other known methodology. Second derivative spectroscopy is the preferred method to quantitatively analyze tryptophan levels as it eliminates background absorbence as, hereinafter, described.

According to an embodiment of the invention, protein-bound tryptophan levels present in the plant material source are enhanced using a series of steps to extract oil from the plant material to render the material partially defatted. The plant source can be a seed such as, for example, but not limited to, butternut squash seed, peppercorn squash seed, pumpkin seed, lentil seed, sunflower seed, flax seed, watermelon seed, sisymbrium seed, cotton seed, sesame seed, canola seed, evening primrose seed, barley, safflower seed, alfalfa seed, soy beans and combinations thereof. Preferably, the seed is a butternut squash seed as it is believed to contain the highest ratio of tryptophan to total proteins, relative to other seed types. The plant source can also be a vegetative part of the plant, such as alfalfa, seaweed or kelp. Although it is preferred to partially defat the plant source to enhance protein-bound tryptophan levels, defatting is not essential to practice the invention.

In a further aspect, the invention provides a method for producing an enriched, natural source of tryptophan, comprising identifying a naturally occurring source of protein-bound tryptophan in a plant source; compressing the plant source under conditions sufficient to release oil contained therein; and at least partially removing the oil contained therein to yield a partially defatted plant source that has a higher tryptophan source than the starting material.

In the case of seeds, it is not necessary to remove their seed coat or hull to expose the endosperm prior to processing. The seed, preferably in one embodiment, is first processed through a series of smooth rollers to produce a thin flake in a process known as flaking. This step allows the oil cells to at least partially rupture and increases the surface area of the seeds for further treatment.

The flaked seeds are subsequently heat treated in a process known as cooking or conditioning to further rupture oil cells and increase the oil viscosity for subsequent defatting. The conditioning step can be performed using, for example, a microwave, an oven or by indirect steam. The temperature of the conditioning step should be sufficient to rupture the oil cells and increase the viscosity of the oil without detrimentally destroying proteins contained in the plant material. Preferably, the temperature is from about 40° C. to about 50° C. The conditioning step is performed for a period of time sufficient to achieve the goal temperature.

Prior to cooling, the heated seed flakes are then mechanically pressed to at least partially remove the oil contained therein. Any known mechanical press or expeller can be used, such as, for example, a Gusta Lab Press. The degree of defatting depends in part on the flaking and cooking steps performed, temperature and oil viscosity and the pressure exerted on the seed. Typically, from about two thirds to about three quarters of the oil is preferably removed.

The pressed plant material can then be further processed depending upon the end user. For example, the plant material can be milled using any conventional means, such as, but not limited to a disk mill, hammer mill or pin mill. The type of mill selected depends in part upon the consistency of the product desired. For example, a pin mill yields a product having a flour-like consistency, while the disk mill or the hammer mill yields a product with a granular consistency.

The hereinabove process yields, according to the invention, a natural source of protein-bound tryptophan having a tryptophan content that is greater than in its parent plant source. Preferably, the material should provide at least 0.2% by weight tryptophan. The resultant, at least partially, defatted seed meal can then be incorporated into compositions useful for inducing sleep.

In addition to the partially defatted meal, the compositions according to the invention further, preferably, comprise a carbohydrate source with a high glycemic index, preferably in the form of glucose, although sucrose and other sugars that breakdown into glucose can be used. Without being bound by theory, it is believed that the carbohydrate source facilitates the uptake of tryptophan per se across the blood brain barrier, where it is made available for metabolism into serotonin. In the human, a barrier exists that allows the brain functions to operate in an independent environment from the rest of the body in order to protect the sensitive nature of the CNS. This barrier is the result of countless tight junctions between the cerebral endothelial cells at the blood-brain interface that restricts diffusion into the brain (Saunders et al., 1991). Superimposed on the diffusion provided by the tight junctions is a series of transport mechanisms into and out of the brain that regulate the internal environment of the brain with respect to a wide range of molecules including electrolytes, glucose, vitamins and amino acids. The transport mechanism for tryptophan is utilized also by other large neutral amino acids (LNAA) as well (Lajtha, 1974; Betz and Goldstein, 1978). Competition for these transport sites, it is believed, is the reason that a large high protein meal fails to induce a hypnotic effect despite containing sufficient tryptophan (Moller, 1983). Conversely, in the same study, high carbohydrate meals with relatively small amounts of tryptophan did induce a mild hypnotic effect. This apparent contradiction may be explained by the shunting of competing LNAA to liver and muscle tissue at times of relatively high insulin serum levels (Fernstrom and Wurtman, 1971). Tryptophan is not shunted in this manner and consequently, any free tryptophan is afforded an insulin-induced competitive advantage of the transport sites across the BBB.

The carbohydrate source, preferably, is present in an amount sufficient to induce an increase in blood insulin levels in the individual consuming the composition. The tryptophan/LNAA ratio increases with increased insulin levels. An increase from 15 microunits/ml to 60 microunits/ml results in an approximately 35% increase in the tryptophan/LNAA ratio. This level of increase is sufficient although less significant increases will also be beneficial. Preferably, the amount of glucose present in the composition is from about 25 g to about 150 g, with 75 g being most preferred. The amount of tryptophan will remain contant but increases in the carbohydrate will increase the tryptophan/LNAA ratio. Other carbohydrate sources may include maltose, sucrose, and the like, but, preferably, not fructose, in view of its low glycemic index. For individuals that are obese or have type II diabetes, a higher amount of carbohydrate e.g., 100 g, may be required because of abnormal insulin responses to glucose.

Since, approximately 80% of tryptophan is protein bound in the blood in vivo, there is only a small pool of free tryptophan that actually competes with other LNAAs for entry into the brain. Consequently, under ordinary conditions plant protein-bound tryptophan that is ingested, is metabolized and, subsequently, quickly stored in the "albumin reservoir" and has little impact on the availability of CNS tryptophan unless given in superphysiological amounts. If, however, tryptophan becomes available at a time when insulin levels increase, free fatty acids compete for the "albumin reservoir" and convert existing protein-bound to free tryptophan, as well as preventing the incorporation of the newly ingested tryptophan. Thus, whilst the serum levels of competing LNAAs are reduced, two separate sources of tryptophan, i.e. existing protein-bound and new ingested tryptophan result in increased free tryptophan. In view of this, it is desirable to provide a product that contains at least some residual oil content to preserve a portion of the fatty acids present in the plant material or seed. For squash seeds, about 20% residual oil remaining in the seed meal is optimal. For other seeds, it may be necessary to add other fatty acids back into the partially defatted product to provide the optimal balance of fatty acids. Hydrogenated oils or other oils, such as canola oil, sunflower oil, safflower oil, palm kernel oil, corn oil or milk solids can be added for this purpose.

In a preferred embodiment, the composition according to the invention comprises at least partially defatted squash seeds, particularly butternut squash seeds, pumpkin seeds, peppercorn seeds and combinations thereof, glucose in an amount sufficient to facilitate uptake of the tryptophan provided from the squash seeds across the blood brain barrier in the individual consuming the composition, and vitamins B3 and B6 in amounts present to facilitate tryptophan uptake.

In another embodiment, the composition comprises at least partially defatted butternut squash seed meal, e.g., from about 50 g to about 100 g, in an amount sufficient to provide about 250 mg to about 1000 mg tryptophan, and from about 25 g to about 200 g glucose. More particularly preferred is a composition comprising from about 25 g to about 50 g defatted butternut squash seed meal pressed to reduce the oil content by 75% and from about 75 g to about 100 g glucose. Optionally, the composition comprises vitamin B3 and/or vitamin B6. Vitamin B3 can be present in amounts of from about 5 mg to about 50 mg; and vitamin B6 in amounts of from about 0.5 mg to about 50 mg, with 50 mg of each of vitamins B3 and B6 being preferred.

The composition and dietary supplements of the invention are intended to be orally administered daily. How the compositions are formulated depends upon the intended use. For example, for sleep augmentation, the compositions may be formulated for single daily administration prior to bedtime. Alternatively, the compositions may be formulated in multiple portions or as time release compositions for more or less frequent administration; for example, the dietary supplement may be formulated as two tablets for twice daily administration, particularly for disorders associated with low serotonin levels. For reasons of size to facilitate ease of swallowing or improved bioabsorption or utilization e.g., before or after a meal or before sleep, a given dosage may be divided into two, three, or more tablets or capsules, and the like. A daily dosage may be administered as one tablet, as two tablets taken together, or as two tablets taken separately e.g., one in the morning and one in the evening. The recommended daily amounts of each ingredient, as described above, serve as a guideline for formulating the dietary supplements of this invention. The actual amount of each ingredient per unit dosage will depend upon the number of units daily administered to the individual in need thereof. This is a matter of product design and is well within the skill of the dietary supplement formulator.

The dietary supplements of the present invention may be formulated using any pharmaceutically acceptable forms of the vitamins, minerals and other nutrients discussed above, including their salts. They may be formulated into capsules, tablets, powders, suspensions, gels or liquids optionally comprising a physiologically acceptable carrier, such as but not limited to water, milk, juice, starch, vegetable oils, salt solutions, hydroxymethyl cellulose, carbohydrate. The dietary supplements may be formulated as powders, for example, for mixing with consumable liquids, such as milk, juice, water or consumable gels or syrups for mixing into other dietary liquids or foods. The dietary supplements of this invention may be formulated with other foods or liquids to provide premeasured supplemental foods, such as single servings bars, for example.

The dietary supplement can be made in a variety of forms, such as baked goods, e.g., cookies, brownies, fudge, cake, breads, biscuits, crackers, puddings, confections, i.e., candy, snack foods e.g., pretzels, chips, dietary beverages, ice cream, frozen confections and novelties, or non-baked, extruded food products such as bars. The preferred form is a non-baked extruded nutritional bar.

The dietary supplement can also contain other ingredients such as one or a combination of other vitamins, minerals, antioxidants, fiber and other dietary supplements. Selection of one or several of these ingredients is a matter of formulation design, consumer and end-user preference. The amount of these ingredients added to the dietary supplements of this invention are readily known to the skilled artisan and guidance to such amounts can be provided by the U.S. RDA doses for children and adults. Vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacin amide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; Vitamin $D_3$; cyanocobalamin; sodium selenite; copper sulfate; Vitamin A; Vitamin E; vitamin $B_6$ and hydrochloride thereof; Vitamin C; inositol; Vitamin $B_{12}$; potassium iodide.

The dietary supplement can comprise one or a combination of antioxidants in therapeutic amounts. Antioxidants suitable for use in this invention include but are not limited to, vitamin, A, vitamin C, vitamin E, ∃-carotene, zinc, chromium, selenium and herbs, such as ginkgo biloba, ginseng. The amount of antioxidant(s) per unit serving are a matter of design and will depend upon the total number of unit servings of the dietary supplement daily administered to the patient. The total amount of antioxidant(s) will also depend, in part, upon the condition of the patient. Preferably the amount of antioxidant(s) will be a fraction or multiplier of the RDA amounts. For example, the dietary supplement will comprise 50% RDA antioxidants per unit dosage and the patient will consume two units per day.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch or toffee. In a preferred embodiment, the dietary supplement contains non-caffeinated cocoa or chocolate, or chocolate substitutes, such as carob. The food compositions may further be coated, for example with a yogurt coating.

Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product.

Preservatives may also be added to the dietary supplement to extend product shelf life. Preferably, preservatives such as potassium sorbate, sodium sorbate, potassium benzoate, sodium benzoate or calcium disodium EDTA are used.

In addition to the carbohydrates described above, the dietary supplement can contain artificial sweeteners, e.g., saccharides, cyclamates, aspartamine, aspartame, acesulfame K, and/or sorbitol. Such artificial sweeteners can be desirable if the dietary supplement is intended for an overweight or obese individual, or an individual with type II diabetes who is prone to hyperglycemia.

To manufacture such a food bar, the liquid ingredients are cooked; the dry ingredients are added with the liquid ingredients in a mixer and mixed until the dough phase is reached; the dough is put into an extruded, and extruded; the extruded dough is cut into appropriate lengths; and the product is cooled. For manufacture of other foods or beverages, the ingredients comprising the dietary supplement of this invention can be added to traditional formulations or they can be used to replace traditional ingredients. Those skilled in food formulating will be able to design appropriate foods/beverages with the objective of this invention in mind.

In a further aspect, the compositions according to the invention can be used to induce sleep in individuals in need thereof. Patients suffering from insomnia, such as caused by stress or side effects of medication can benefit from the compositions described herein. Further, the compositions can be used as an adjunct in the treatment of psychiatric disorders by providing a tryptophan source that can be transported to the brain and metabolized into serotonin. Thus, the compositions can be used to ameliorate the effects of reduced serotonin levels in an individual which manifest as depression, anxiety disorders, obsessive compulsive disorders, pain disorders, aggression and eating disorders. The daily recommended amount of tryptophan would depend in part on the medical reason for tryptophan supplementation, the age and condition of the individual and medication(s) the individual is/are taking. The practitioner would be able to evaluate these factors and determine the proper recommended dosage.

The hypnotic effects of tryptophan are well studied and follow a fairly flat dose-response curve (for review see Schneider-Helmut and Spinweber, 1986). When given alone, 1 gm of tryptophan a.i. is sufficient to produce improved sleep in the majority of people with mild insomnia. Higher dosages (2–12 gm) offer little extra benefit and indeed at the highest dosages (12 gm) sleep was disrupted despite a reduction in sleep latency (Griffiths et al., 1972). Later studies show that dosages greater than 1 gm do not significantly shorten the sleep latency but are associated with a subjective experience of drowsiness (George et al., 1989). Wyatt and colleagues (1970) were the first to describe that ongoing use of tryptophan leads to an increase in Total Sleep Time (TST) which persists for days after the tryptophan treatment is discontinued. In psychiatric conditions as little as 250 mg of tryptophan per day can aid in increasing the concentration of serotonin offering significant clinical improvement.

It is noted that there are potential side effects with tryptophan supplementation. Tryptophan at lower dosages have few side effects but there are reports of difficulties at higher dosages or in combination with certain antidepressants. When combined with a monoamine oxidase inhibitor (MAOI), tryptophan carries a risk of delirium and neurological dysfunction (Thomas and Rubin, 1984). At higher dosages (greater than 12 gm per day) the most frequent complaints are daytime sedation and nausea (Hartmann, 1977). There are a few theoretical risks that have been demonstrated in animal models but not in humans. Large dosages of 1-tryptophan produce lipogenesis in animals (Fears and Murrell, 1980) but this effect was not seen in humans (Sourkes, 1983). Similarly there is a theoretical risk that a tryptophan metabolite, xanthurenic acid may lead to the development of diabetes (Kbtake and Murakami, 1971). Thus, it is an objective of the present invention to limit the daily amount of protein-bound tryptophan administered to an individual to levels below about 12 g tryptophan a.i. per day to avoid these potential side effects.

In yet a further aspect, the invention provides a process for the manufacture of a pharmaceutical composition when used for inducing sleep in a human said process comprising admixing a composition as hereinbefore defined with a pharmaceutically acceptable carrier therefore.

BRIEF DESCRIPTION OF THE DRAWINGS

In order that the invention may be better understood, preferred embodiments will now be described by way of example only with reference to the accompanying drawings, wherein FIG. 1. is a graph of sleep efficiency % over pre-, post- and treatment periods with (a) partially defatted meal containing protein-bound tryptophan according to the invention and (b) pharmaceutical grade tryptophan per se.

DETAILED DESCRIPTION OF PREFERRED EMBODIMENTS

EXAMPLES

Example 1

Figure 1:
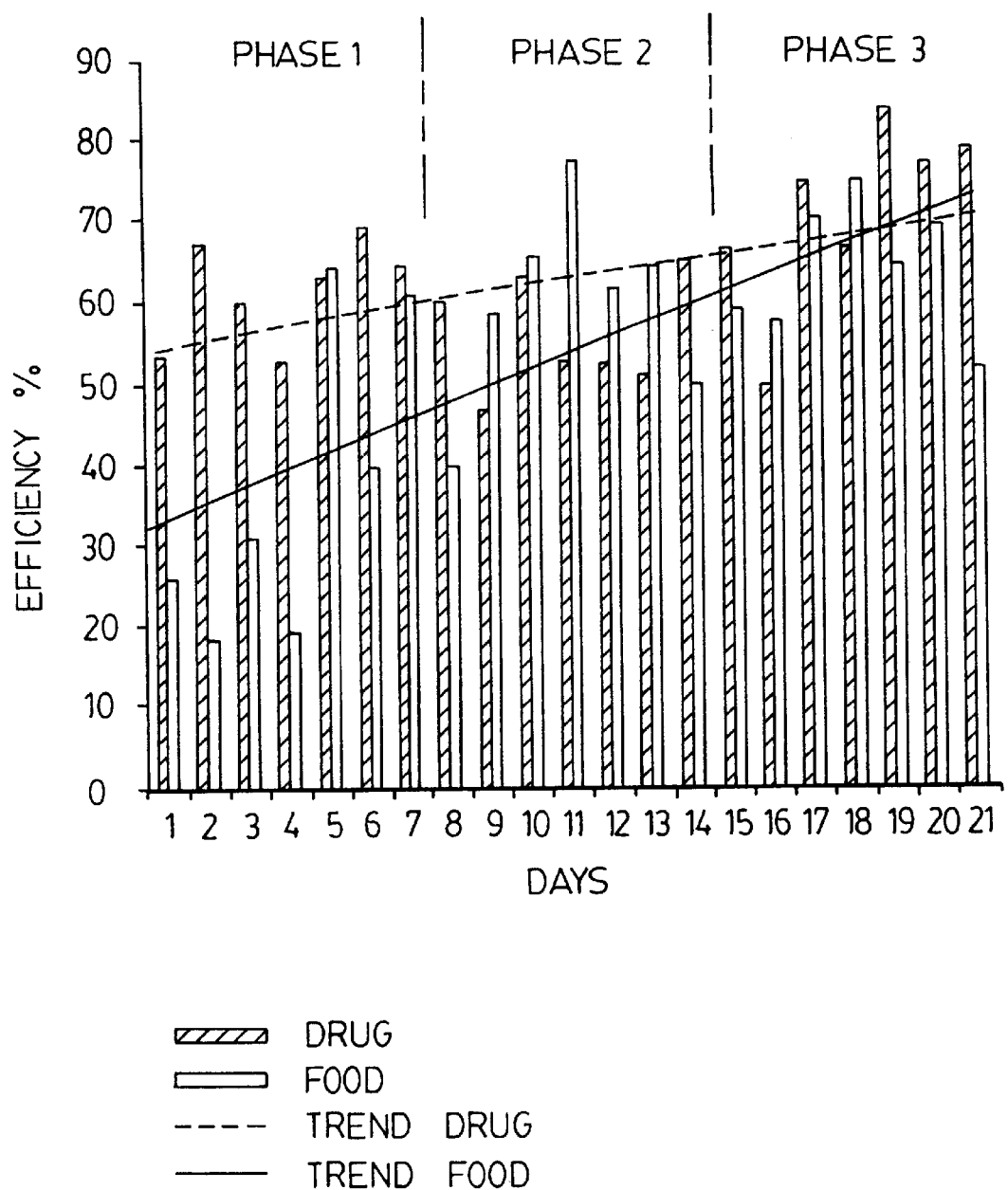

Procedure for Defatting seeds Using a Modified Oil Press

Flaking

Initial flaking of the squash seeds is done to rupture oil cells and to prepare a thin flake with a large surface area for pre-pressing by passing seeds through a set of smooth rollers using a lab scale flaking mill.

Conditioning

Conditioning is done to further rupture oil cells, increase pliability of the flakes and increase the efficiency of the expeller by lowering the viscosity of the oil contained. The conditioning of the flaked seeds was undertaken in a microwave for from about 1 minute to about 2 minutes to achieve a temperature between 40–45° C.

Pressing

The heated seeds are then pressed using a mechanical press (Gusta Laboratory Press set to 4.5 amps) to remove approximately ⅔ oil with 22% by weight residual oil content in the press cake.

Example 2

Tryptophan Analysis of the Defatted Seed Meal

A. High Pressure Liquid Chromatography (HPLC)

With pure protein or peptides, amino acid determination is relatively easily made with High Pressure Liquid Chromatography (HPLC). HPLC requires the hydrolysis of protein into the constituent amino acids that are then run in a column under pressure. The column causes the various amino acids to run at different speeds dependent on the size and charge. The determination of a tryptophan within a food source is, however, more complicated because of its ability, especially in the peptide form, in the presence of light, heat, hydrogen and hydroxyl ions (Concon, 1975). This difficulty may explain, in part, the problems in quantifying tryptophan within food in a reliable fashion utilizing HPLC with possible tryptophan losses of 10–30% (Landry and Delhaye, 1996). Relying on the presence of an aromatic ring within the tryptophan molecule, a spectrophotometric method was utilized at the Guelph Food Technology Centre that allowed for the reliable quantification of tryptophan (Balestrierl et al., 1978).

B. Second Derivative Spectroscopy

The quantitative determination of aromatic amino acids in proteins is possible with second derivative spectroscopy, an analysis of the ultraviolet absorption spectra within a certain wavelength. Derivative spectroscopy is superior to direct spectroscopy through the elimination of spectral interference. In the case of tryptophan, direct spectroscopy produces a sloping background absorbence. Second derivative spectroscopy eliminates any background absorbence allowing the tryptophan absorbence to be quantified at a wavelength of approximately 280 nm.

Example 3

Comparative Analysis of Defatted Pumpkin, Butternut and Peppercorn Squash Seeds Pumpkin seeds, butternut squash seeds and peppercorn squash seeds were flaked, conditioned and pressed according to the procedure set forth in Example 1. Using second derivative spectroscopy, the tryptophan content of the seed meal was determined and the results set forth in the Table below. Screening of butternut squash, peppercorn squash and pumpkin seeds revealed that all have high tryptophan contents but that butternut squash seeds are highest in tryptophan. It also revealed that 100 gm of defatted butternut squash seed meat contains in excess of 1000 mg of tryptophan. For butternut squash, the ratio of seeds to the fmal seed meal is approximately one third.

TABLE

| Source | Tryp/Total Protein(mg/g) | Tryp/defatted meal(protein, starch, fiber) (mg/g) | Oil (g/kg) | Crude Protein (g/kg) (intact seed) |
|---|---|---|---|---|
| Pumpkin seed defatted meal | 17.9 | 7.35 | 333 | 208 |
| Butternut squash seed defatted meal | 23.8 | 10.1 | 403 | 221 |
| Pepper squash seed meal | 17.9 | 8.14 | 446 | 202 |

HPLC analysis on partially dehulled and partially defatted butternut squash seeds are as follows:

Valine—1.445%

Isoleucine—1.115%

Leucine—2.111%

Tyrosine—1.316%

Phenylalanine—1.481%

Controlled Tripartite Double Blind Sleep Study of Sleep Food Overview

Tryptophan content of food is typically determined with high pressure liquid chromatography (HPLC) in which the protein undergoes base hydrolysis into its constituent amino acids over several hours. In the context of food analysis this methodology can lead to a 10–30% loss of tryptophan (Landry and Delhaye 1996). To avoid this potential problem second derivative-spectroscopy, a method to screen various seeds without the need for protein hydrolysis at high temperatures over prolonged periods (Balestrierl et al 1978) was used. The results of these tests revealed that seed of the butternut squash contains more tryptophan than any other reported food source. In fact, the protein portion of the seed contains 25 mg of tryptophan per 1 g of protein. Since HPLC is the industry standard, a sample of defatted butternut squash seeds was analyzed with HPLC after NaOH hydrolysis in an argon environment. The high content of tryptophan in these seeds was determined, although the predicted loss of some tryptophan with hydrolysis was also confirmed. The concentration of tryptophan was sufficient to provide a plant-based functional food that acts as a natural source of Central Nervous System (CNS) tryptophan.

Study Design

A three arm study was run in parallel with subjects randomly assigned to one of three groups, namely (a) a food rich in defatted squash meal in combination with a carbohydrate; (b) a food enriched with pharmaceutical grade tryptophan and a carbohydrate; and (c) a placebo food rich in a carbohydrate with minimal protein. Both the subject and the research nurse who conducted the study were blind to the assignment of each subject. The subjects met the nurse on a weekly basis in order to turn in their sleep scores and review any side effects from that week and to receive the sleep diary for the next week.

Food Composition

Food1 was prepared in a 7 day lot according to the following amounts:

150 ml of sweetened, condensed milk 100 gm glucose 60 gm butter 2 gm salt 160 gm defatted squash seed 90 gm graham crackers 80 gm butterscotch chips 10 ml vanilla 200 mg Vitamin B3
250 mg B6

Food2 was prepared in a 7 day lot according to the following amounts:
150 ml of sweetened, condensed milk
100 gm glucose
60 gm butter
2 gm salt
1500 mg pharmaceutical grade tryptophan
160 gm rolled oats
80 gm butterscotch chips
10 ml vanilla
200 mg B3
250 mgB6

Food3 was prepared in a 7 day lot according to the following amounts:
150 ml defatted (1%) milk
120 gm. butter
10 gm nutrasweet
30 gm nutrasweet cocoa powder
160 gm rolled oats
20 gm. ground kidney beans
2.5 ml vanilla Sleep Protocol Each subject completed three weeks of study.

Week 1 allowed for a baseline measurement of sleep parameters as determined by a structured sleep diary (Morin 1993a). Sleep parameters measured included Total Time Awake each night, Total Sleep Time each night, Total Time in Bed each night, Sleep Efficiency (Total Sleep Time/Total Time in Bed×100). Subjects completed a sleep quality assessment as determined by the Sleep Impairment Index (Morin 1993b) at the beginning and end of the first week. They also recorded their previous nights sleep patterns every morning in the structured sleep diary.

In Week 2, defined as the treatment week, each subject ingested food1, food2 or food3 depending on their assignment, one hour prior to bed. Subjects continued to report their sleep in the structured sleep diary each morning and again completed the Sleep Impairment Index at the conclusion of the week.

Week 3, each subject continued to record their sleep each morning in the structured sleep dairy but in the absence of the assigned food. At the conclusion of week 3 and the study, they again completed the Sleep Impairment Index.

Subjects

Criteria for selection included men and women over the age of 18 experiencing trouble falling asleep or staying asleep three or more nights/week for a duration of three months. Exclusion criteria included heart disease, pregnancy, food allergies, diabetes, sleep apnea, and shift workers.

A sample of volunteers was selected from Perth County region, Ontario, Canada. One hundred and fifty eight (158) subjects were recruited through letters to family doctors, newspaper and radio advertisement. Fifty-one subjects were rejected after a short (approximately 10 minute) structured telephone interview indicating evidence of health issues, medication or lack of desire to commit to the three week protocol. A further 50 subjects were rejected after a detailed structured personal interview with a research nurse for the following reasons: health (20); failure to appear for the interview (3); medication contraindicated with tryptophan (12); unwillingness to stop sleep medications (3); food allergies (5), unwillingness to commit to three week protocol (3), shift workers (3), inability to meet criteria for insomnia (1).

After initiation into the study, seven subjects failed to complete the protocol for the following reasons: time commitment (1), failure to attend weekly interviews (1), death of close family member (1), relationship stress (1), nausea (1 food1, 2 placebo).

All subjects were assessed by the following: Brief Symptom Inventory (BSI), a medical and psychiatric interview, and laboratory tests as deemed necessary by the principal investigator (i.e. blood tests, urinalysis, EKG etc).

All subjects were informed about the purpose, risks and benefits associated with the study. Written, signed consent was obtained and a copy given to the participant. Subjects were asked to abstain from the use of alcohol, during the entire three week study. They were instructed to limit their caffeine intake and to maintain a regular sleep wake schedule during this period. Ethical approval was given from the ethics committee of the Stratford General Hospital.

Twin Study

Coincidentally two identical twin brothers enrolled in the study apparently unaware that each other had also enrolled. These twin subjects were randomly assigned to one of the two treatment conditions of food1 and food2. Their data is included in the grouped data but was also analyzed separately. The twin brothers were 56 years old, of similar weight (68.2 vs. 70.5 kg) and in good physical health. Both identified significant difficulties with initiating and maintaining sleep of a long-standing duration.

Method

For a preliminary study a total of 29 subjects (22 females, 7 males) were randomly assigned to one of three treatment conditions: food1, defatted butternut squash seed meal in combination with glucose, vitamin B3 and B6; food2, 220 mg of pharmaceutical grade tryptophan in a food rich in carbohydrate (including an equivalent amount of glucose contained in food1), vitamins B3 and B6 with; food3 (placebo), carbohydrate with a trace amount of protein. The average ages (52.1, 49.5 and 54.4 years, respectively) did not differ significantly between groups. The average weight (72.3, 67.1 and 72.9 kg.) did not significantly differ between groups.

In a second study (which incorporated data from the preliminary analysis) a total of 50 subjects (38 females, 12 males) were randomly assigned to one of three treatment conditions described above: food1, food2 and placebo, carbohydrate with a trace amount of protein. The average ages (53.3, 52.1, 50.1 years) did not differ significantly between groups. The average weight (71.0, 71.6, 71.8 kg.) did not significantly differ between groups.

Results

A Multivariate Analysis of Variance (MANOVA) with 3 between factors (food 1, food2 and placebo) and 3 within factors (week1-baseline, week2-treatment, and week3-post-treatment) did not result in any significant interactions in the preliminary analysis of 29 subjects. Significant differences, however, were noted between baseline and treatment weeks in the following sleep parameters: sleep efficiency, total wake time and total sleep time. These differences are summarized in the tables 3, 4 and 5 below.

The same 3×3 MANOVA when performed on data from the 50 subjects resulted in a week (baseline, treatment, post-treatment) by condition (food1, food2, placebo) interaction (p=0.03). Post hoc analyses revealed that this interaction resulted from a significant reduction in total time in bed in week2 (treatment week) for those treated with food1 in contrast to an increase in time in bed during the treatment week for food2 and placebo.

Total Time in Bed

Total time in bed measures the time from bedtime to rising time and includes time to fall asleep, time asleep, time awake during the night and time waiting in bed after awaking but before rising. As described above subjects treated with food1 had a significant reduction in total time in bed in contrast to an increase for food2 and placebo. The differences in total time in bed their significance are recorded in Table 1.

more continuous block of sleep. Therefore, sleep interruption time, a sleep parameter specific to the determination of a continuous block of sleep, was analyzed in addition to other sleep variables which were included in the preliminary study: sleep efficiency, total wake time and total sleep time.

Sleep Interruption Time

Sleep interruption time measures the amount of time awake during the night as the result of an interrupted sleep pattern. The results indicate that there is a significant reduction (average reduction of 23 minutes/night) in time lost due to sleep interruptions for those treated with food1 which was significantly different from baseline (p=0.006) as well as the placebo (p=0.04). Those subjects treated with food2 also had a reduction of 15 minutes which was different from baseline (p=0.003) but not placebo. The results are summarized in Table 2.

TABLE 1

Total Time in Bed

| Food | Week 1 (Mean ± s.e.) mins. | Week 2 (Mean ± s.e.) mins. | Decrease during treatment (mins.) | Week 3 (Mean ± s.e.) | Decrease (mins.) | Total Decrease (mins.) |
|---|---|---|---|---|---|---|
| Food1 (Squash based food) | 491 + 12.2 | 481 + 12.1 | 9.6 + 4.7 (p = .048) | 483 ± 12 | Increase 2 mins (p = 0.78) | 8 mins (p = 0.146) |
| Food2 (Pharm. Tryp.) | 474 + 12.9 | 481 + 12.8 | Increase 6.5 + 5.0 (p = .202) | 471 ± 13 | 10 mins (p = 0.10) | 3 mins (p = 0.580) |
| Food3 (Placebo) | 482 + 13.4 | 489 + 13.2 | Increase 7.6 + 5.2 (p = .149) | 494 ± 13 | Increase 5 mins (p = .39) | Increase 12 mins (p = .037) |

Table 1 shows that Food1 results in significantly less time in bed in comparison to both placebo (p = 0.02) and Food2 (p = 0.02).

Further analyses suggest that this difference may result from the fact that those subjects treated with food1 had a

TABLE 2

Sleep Interruption Time

| Food | Week 1 (Mean ± s.e.) mins. | Week 2 (Mean ± s.e.) mins. | Decrease during treatment (mins.) | Week 3 (Mean ± s.e.) | Decrease (mins.) | Total Decrease (mins.) |
|---|---|---|---|---|---|---|
| Food1 (Squash based food) | 59 ± 9.7 | 36 ± 7.3 | 23 ± 8.1 (p = .006) | 37 ± 6.6 | Increase 1 mins (p = 0.862) | 22 mins (p = 0.005) |
| Food2 (Pharm. Tryp.) | 58 ± 10 | 43 ± 7.7 | 15 ± 8.6 (p = .003) | 45 ± 7.0 | Increase 2 mins (p = 0.805) | 13 mins (p = 0.106) |
| Food3 (Placebo) | 51 ± 11 | 53 ± 8.0 | Increase 1.7 ± 8.9 (p = .523) | 44 ± 7.3 | 9 mins (p = .236) | 6 mins (p = .421) |

Table 2 shows that Food1 performed significantly better than placebo p = 0.04.

Total Wake Time

In a preliminary study (n=29), during the treatment week, the squash (food1) decreased the total wake time by 41 minutes/night on average (p=0.011) which was greater than the food enriched with pharmaceutical grade tryptophan (food2) which decreased the total wake time by 30 minutes (p=0.040). The carbohydrate placebo (food3) decreased the wake time by 5 minutes which was not statistically significant (p=0.760).

In the post-treatment there was only a modest further reduction in each group which was not significantly significant. Table 3 summarizes the change in total wake time.

TABLE 3

Total Wake Time

| Food | Week 1 (Mean ± s.e.) mins. | Week 2 (Mean ± s.e.) mins. | Decrease (mins.) | Week 3 (Mean ± s.e.) | Decrease (mins.) | Total Decrease (mins.) |
|---|---|---|---|---|---|---|
| Food1 (Squash based food) | 133 ± 21 | 91 ± 18 | 41 (p = .011) | 89 ± 16 | 3 (p = 0.854) | 44 (p = .003) |
| Food2 (Pharm. Tryp.) | 167 ± 19 | 138 ± 16 | 30 (p = .040) | 129 ± 15 | 9 (p = 0.49) | 39 (p = .004) |
| Food3 (Placebo) | 118 ± 21 | 113 ± 18 | 5 (p = .760) | 99 ± 16 | 14 (p = .336) | 19 (p = .179) |

In the complete study, during the treatment week, the squash (food1) decreased the total wake time by 30 minutes/night on average (p=0.008) whereas the food enriched with pharmaceutical grade tryptophan (food2) also decreased the total wake time from baseline by 35 minutes (p=0.003). The carbohydrate placebo (food3) decreased the wake time by only a marginal amount (7.5 minutes) which was not statistically significant (p=0.523). The advantage of the food1 and food2 treatment is lost in the post-treatment week. Table 3a summarizes the change in total wake time.

TABLE 3a

Total Wake Time

| Food | Week 1 (Mean ± s.e.) mins. | Week 2 (Mean ± s.e.) mins. | Decrease during treatment (mins.) | Week 3 (Mean ± s.e.) | Decrease (mins.) | Total Decrease (mins.) |
|---|---|---|---|---|---|---|
| Food1 (Squash based food) | 154 ± 16 | 124 ± 15 | 30 (p = .008) | 121 ± 14 | 3 (p = .722) | 33 (p = .002) |
| Food2 (Pharm. Tryp.) | 159 ± 17 | 124 ± 16 | 35 (p = .003) | 130 ± 15 | Increase 6 (p = .608) | 29 (p = .011) |
| Food3 (Placebo) | 122 ± 18 | 114 ± 16 | 7.5 (p = .523) | 94 ± 16 | 20 (p = .091) | 28 (p = .018) |

Sleep Efficiency

In a preliminary study, during the treatment week both the squash (food1) and the food enriched with pharmaceutical grade tryptophan (food2) improved sleep efficiency. Squash (food1) increased sleep efficiency by 8%/night (p=0.013) whereas the food enriched with pharmaceutical grade tryptophan increased by 5%/night (p=0.047). The carbohydrate placebo (food3) also increased sleep efficiency by only 1% (p=0.749).

In the post-treatment when all three groups were no longer eating an experimental food, advantage of both squash and pharmaceutical grade tryptophan was lost. Table 4 summarizes the comparisons of sleep efficiencies.

TABLE 4

Sleep Efficiency

| Food | Week 1 (Mean ± s.e.) % | Week 2 (Mean ± s.e.) % | Increase % | Week 3 (Mean ± s.e.) | Increase % | Total Increase % |
|---|---|---|---|---|---|---|
| Food1 (Squash based food) | 73 ± 4 | 81 ± 3 | 8 (p = .013) | 82 ± 5 | 1 (p = 0.839) | 9 (p = .112) |
| Food2 (Pharm. Tryp.) | 66 ± 4 | 71 ± 3 | 5 (p = .047) | 72 ± 5 | 1 (p = 0.785) | 6 (p = .177) |
| Food3 (Placebo) | 76 ± 4 | 77 ± 3 | 1 (p = .749) | 90 ± 5 | 13 (p = .018) | 14 (p = .017) |

In a complete study, during the treatment week both the squash (food1) and the food enriched with pharmaceutical grade tryptophan (food2) improved sleep efficiency. Squash (food1) increased sleep efficiency by 5%/night (p=0.019) whereas the food enriched with pharmaceutical grade tryptophan increased by 8%/night (p=0.002). The carbohydrate placebo also increased sleep efficiency by only 2% (p=0.369). Table 4a summarizes the comparisons of sleep efficiencies.

TABLE 4a

Sleep Efficiency

| Food | Week 1 (Mean ± s.e.) % | Week 2 (Mean ± s.e.) % | Increase % | Week 3 (Mean ± s.e.) | Increase % | Total Increase % |
|---|---|---|---|---|---|---|
| Food1 (Squash based food) | 69 ± 3 | 74 ± 3 | 5 (p = .019) | 75 ± 3 | 1 (p = .839) | 6 (p = .007) |
| Food2 (Pharm. Tryp.) | 67 ± 3 | 75 ± 3 | 8 (p = .002) | 73 ± 3 | Decrease 2 (p = .414) | 5 (p = .02) |
| Food3 (Placebo) | 75 ± 3 | 77 ± 3 | 2 (p = .369) | 81 ± 3 | 4 (p = .10) | 6 (p = .01) |

Total Sleep Time

In the preliminary study the total sleep time was increased across all three conditions but especially so in those subjects treated with food1 and food2. Only those treated with food2 actually had a statistically significant increase in sleep time (p=0.04) although the increase in sleep time in those treated with food1 approached statistical significance (p=0.066). The increase in sleep time in those treated with placebo did not approach statistical significance (p=0.520). These results are summarized in Table 5.

TABLE 5

Total Sleep Time

| Food | Week 1 (Mean ± s.e.) mins. | Week 2 (Mean ± s.e.) mins. | Increase (mins.) | Week 3 (Mean ± s.e.) | Increase (mins.) | Total Increase (mins.) |
|---|---|---|---|---|---|---|
| Food1 (Squash based food) | 359 ± 20 | 389 ± 22 | 30 (p = .066) | 394 ± 16 | 6 mins (p = 0.72) | 36 mins (p = 0.039) |
| Food2 (Pharm. Tryp.) | 304 ± 18 | 334 ± 20 | 30 (p = 0.044) | 337 ± 15 | 3 mins (p = 0.86) | 33 mis (p = 0.039) |
| Food3 (Placebo) | 364 ± 20 | 374 ± 22 | 10 (p = .520) | 398 ± 16 | 24 mins (p = .143) | 34 mins (p = .143) |

In a complete study the results paralleled those of the preliminary study. Those subjects treated with food2 had a statistically significant increase in sleep time during the treatment week and those treated with food1 had an increase that approached statistical significance. These results are summarized in Table 5a.

doubled his sleep efficiency over the course of the study. The twin treated with pharmaceutical grade tryptophan per se increased his sleep efficiency by less than 30%.

Increases in sleep efficiency paralleled the increases in total sleep time. The twin treated with the squash based food more than doubled his total nightly sleep whereas as his twin TABLE 5a Total Sleep Time

| Food | Week 1 (Mean ± s.e.) mins. | Week 2 (Mean ± s.e.) mins. | Increase (mins.) | Week 3 (Mean ± s.e.) | Increase (mins.) | Total Increase (mins.) |
|---|---|---|---|---|---|---|
| Food1 (Squash based food) | 340 ± 15 | 358 ± 15 | 19 (p = .098) | 361 ± 13 | 3 mins (p = 0.773) | 22 mins (p = 0.065) |
| Food2 (Pharm. Tryp.) | 315 ± 16 | 356 ± 16 | 42 (p = 0.001) | 342 ± 14 | Increase 15 mins (p = 0.223) | 27 mins (p = 0.032) |
| Food3 (Placebo) | 359 ± 17 | 376 ± 17 | 17 (p = .167) | 401 ± 15 | 25 mins (p = .049) | 42 mins (p = .002) |

Subjective Results

Subjects recorded their subjective response based on a weekly report of the Sleep Impairment Index. A seven-point questionnaire self-rating scale analyzed various aspects of insomnia and its impact on daily function.

Eleven of 18 subjects (61%) treated with food1 reported less concern about their sleep after one week of treatment in comparison to 6 of 17 subjects treated with food2 (35%) and 5 of 15 subjects treated with placebo (33%).

The overall perception of one's state upon waking each morning was also measured on a daily basis. This question assessed their overall perception of their waking state on a three-point scale, with 1 as 'exhausted' and 3 as 'refreshed'. Those subjects treated with the squash-based food (food1) reported a highly significant improvement. These differences and their significance are summarized in Table 6.

treated with pharmaceutical grade tryptophan increased his total nightly sleep by less than 35%. Further studies were carried out which measured not only the actual parameters of sleep disturbance but also the impact of insomnia on daily lives. The subjective and objective measures that resulted in significant results are described below.

Comparison on Defatted Meal Alone

A subset of subjects was drawn to ingest defatted squash seed meal without any other additive. After the conclusion of their 21-day original trial, each if these subjects underwent a 4-week washout period. At the conclusion of the washout period each subject was given 22 gm of defatted squash seed meal/night with instructions to follow the original protocol (eat experimental food 1 hour prior to bedtime, following the sleep pattern described above, avoidance of protein in the evening meal etc.). One subject was

TABLE 6

AM Quality

| Food | Week 1 (Mean ± s.e.) | Week 2 (Mean ± s.e.) | Percent Increase During treatment | Week 3 (Mean + s.e.) | Increase | Total Increase |
|---|---|---|---|---|---|---|
| Food1 (Squash based food) | 1.78 + .09 | 2.03 + .09 | .248 (p = .006) | 1.89 + .09 | Decrease .133 (p = .067) | .115 (p = .09) |
| Food2 (Pharm. Tryp.) | 1.88 + .09 | 2.13 + .09 | .246 (p = .01) | 2.05 + .09 | .084 (p = .09) | .161 (p = .07) |
| Food3 (Placebo) | 1.63 + .1 | 1.78 + .11 | .149 (p = .12) | 1.89 + .1 | .113 (p = .220) | .262 (p = .001) |

Twin Study Analysis

Figure 2:
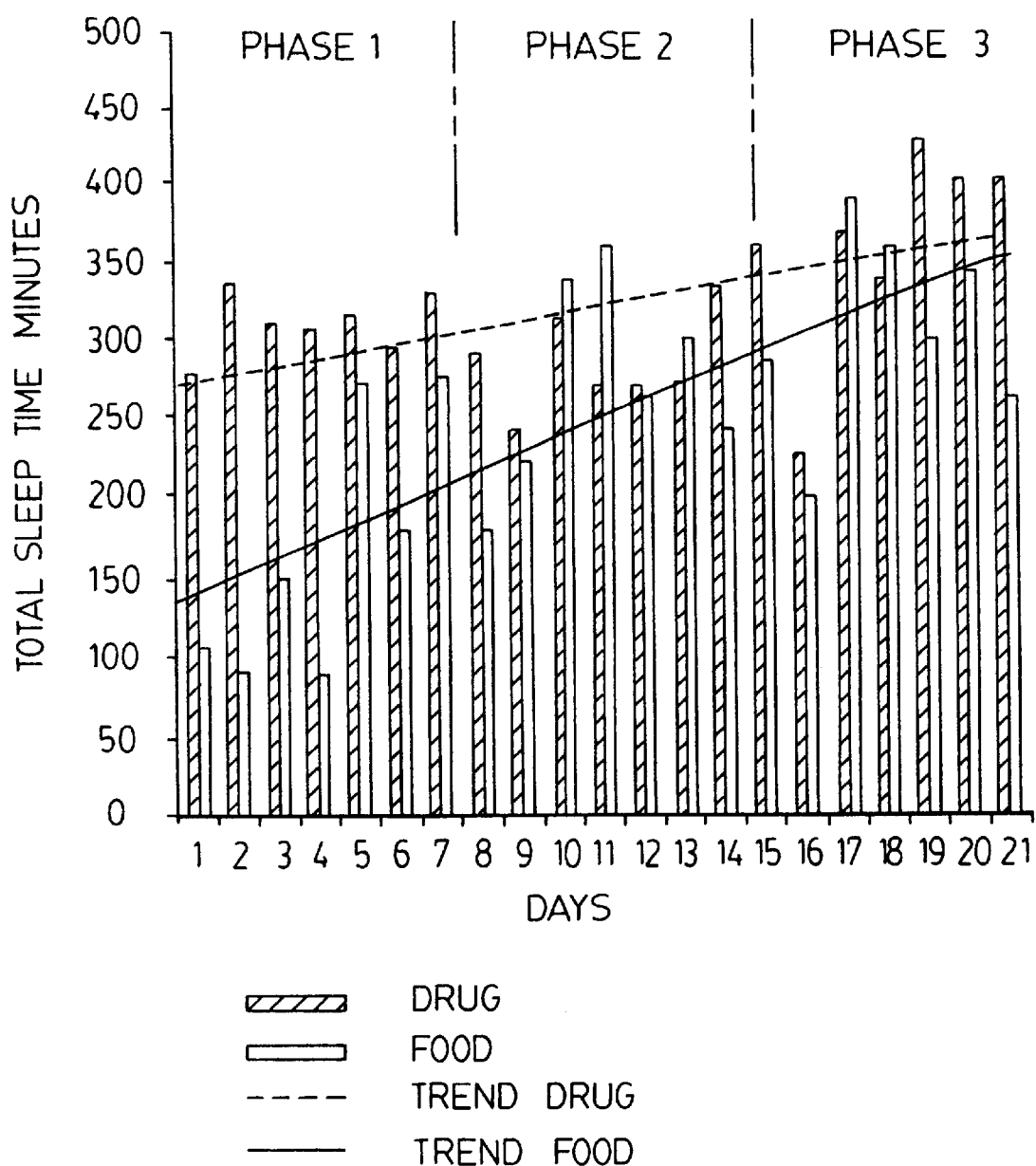
FIG. 2. is a graph of total sleep time over pre-, post- and treatment periods with (a) partially defatted meal containing protein-bound tryptophan according to the invention, and (b) pharmaceutical grade tryptophan per se.

With reference to FIGS. 1 and 2, phases 1 and 3 represent non-treatment seven day periods, i.e. pre-and post-treatment seven day periods, respectively.

The identical twin in the squash (food1) treatment outperformed his sibling treated with pharmaceutical grade tryptophan (food2) on both a reduction of total wake time as well as increased sleep efficiency throughout the study. A sample size of two does not allow statistical analysis so graphs of outcome are included instead with trend lines included. The most apparent differences occurred in total sleep time wherein the twin on squash food more than excluded after she reported adding a carbohydrate to the defatted meal despite instructions to the contrary.

The remaining number was too small to allow for valid statistical analysis but there was an overall reduction in average Total Wake Time (114.7 mins, baseline vs. 59.7 mins with defatted meal), an increase in Total Sleep Time (385.4 mins, baseline vs. 411.7 with defatted meal) and an increase in Sleep Efficiency (76.5% baseline vs. 87% with defatted meal).

Discussion

The apparent superior performance of food1 based on squash seed defatted meal is, indeed, surprising. In fact, previous experiments would suggest that the plant protein should have resulted in an inferior performance to the combination of pharmaceutical grade tryptophan and carbohydrate. In a seminal study of diet and brain tryptophan levels, Fernstrom and Wurtman (1972) fed six groups of rats one of six meals prior to their sacrifice: (i) diet 1, carbohydrate meal (ii) diet 2, diet 1 supplemented with 18 percent casein, dry weight (iii) diet 3, diet 1 supplemented with an artificial amino acid similar to casein in amino acid content, 18 percent dry weight (iv) diet 3, minus tyrosine, phenylalanine, leucine, isoleucine, and valine. Groups of rats were killed 1 or 2 hour postprandial to determine plasma tryptophan, brain tryptophan and brain serotonin levels. Subsequent analysis demonstrated that although protein meals result in a significant rise (60–70%) in plasma tryptophan there was no significant increase in brain tryptophan or serotonin. Further study of an additional two groups of rats (one fed diet 3 with the complete amino acid mixture versus another fed diet 3 with a complete amino acid mixture minus tyrosine, phenylalanine, leucine, isoleucine and valine) found a significant increase in brain tryptophan occurred only in the diet minus the competing neutral amino acids. Although the time course to sacrifice was relatively short in the Fernstrom and Wurtman's experiment, a later experiment (Fernstrom et al. 1985) sacrificed rats every 4 hours postprandial over a 24 hour period and also failed to find any significant increase in brain tryptophan at any point in a 24 cycle after the ingestion. In this later experiment some rats were fed significant quantities in protein (maximum of 40% protein diet) which lead to significant increases in serum tryptophan but no change in brain tryptophan levels.

Investigations in non-human primates parallel those findings from rat studies in that conditions that favour increased ratio of serum tryptophan/competing amino acids results in increased brain tryptophan. Leathwood and Fernstrom (1990) demonstrated a dose-dependent increase in tryptophan in subcortical regions of the brain, in concert with a dose-dependent reduction in competing amino acids, when groups of adult cynomolgus monkeys were fed various combinations of carbohydrate (maltodextrin) and one of three amounts of synthetic tryptophan (20 mg/kg, 90 mg/kg and 400 mg/kg).

Thus, a fair and thorough review of the literature would predict the superiority of pharmaceutical grade tryptophan per se combined with carbohydrate over placebo and squash meal. The present squash seed food formulation contains defatted meal which is rich in protein and therefore should not result in equivalent or superior sleep based upon previous animal studies. Similarly, the defatted meal alone appears beneficial which again is not obvious based upon the previous literature since defatted meal is approximately 47% protein by weight and less than 15% carbohydrate.

The previous literature would predict the clear advantage pharmaceutical grade tryptophan in combination carbohydrate in the improvement of sleep. The fact that defatted seed meal is superiour to pharmaceutical grade tryptophan is surprising and may reflect differences in human brain function in comparison to other mammalian brains (both primate and non-primate), some beneficial effect in the ingestion of a protein rich in the tryptophan precursor, or some other metabolic advantage. It may also be concluded that either other amino acids in the protein actually assist in sleep enhancement or some other aspect of protein ingestion in humans affects the transmission of tryptophan across the blood-brain-barrier in a way not predicted by ratio of serum tryptophan to other competing amino acids.

References

Betz A. L. and Goldstein, G. W., *Science*, 202:225–227 (1978).
Boman, B., Aust. NZ J. *Psychiatry*, 22:83–97 (1988).
Balestriel, C., et al., *European Journal of Biochemistry*, 90:433–440 (1978).
Fears, R., and Murrell, F. A., *British Journal of Nutrition*, 43:349–356 (1980).
Fernstrom, J. D. and Wurtman, R. J, *Science*, 174:1023–1025 (1971).
George, C. F., et al., *Sleep*, 12:345–53 (1989).
Griffiths, W. L., et al., *Psychobiology*, 9:345–356 (1972).
Hartmann, E., *American Journal of Psychiatry*, 134:366–370 (1977).
Kotake, Y. and Murakami, E., *American Journal of Nutrition American Journal of Clinical Nutrition*, 24:826–829 (1971).
Lajtha, A., In *Aromatic Amino Acids in the Brain* (CIBA Foundation Symposium 22) New York: American Elsevier pp. 25–49 (1974).
Moller, S. E., *Human Neurobiology*, 2:41–8 (1983).
Sourkes, T. L., *Advances in Biological Psychiatry*, 10:160–173 (1983).
Schneider-Helmet, D. and Spinweber, C. L., *Psychopharmacology*, 89:1–7 (1986).
Saunders, N. R., et al., *Clinical and Experimental Pharmacology and Physiology*, 26:11–19 (1999).
Thomas, J. M. and Rubin, E. H., *American Journal of Psychiatry*, 141:281–283 (1977).
Wyatt, R. J. et al., *Lancet II*, 84:842–846.(1970).
Balestrierl C, Colonna G, Giovans A, Irace G, Servillo L L (1978) Second-derivative spectroscopy of proteins: a method for the quantitative determination of aromatic acids in proteins European Journal of Biochemistry 90: 433–440
Fernstrom J D Wurtman R J (1972) Brain serotonin content: physiological regulation by plasma neutral amino acids. Science 178: 414–6
Fernstrom J D Fernstrom M H Grubb P E Volk E A (1985) Absence of chronic effects of dietary protein content on brain tryptophan concentrations in rats. Journal of Nutrition 115: 1337–44
Griffiths W J, Lester B K, Coulter J D, Williams H L (1972) Tryptophan and sleep in young adults. Psychophysiology 9: 345–356
Hartmann E (1982) Effects of L-tryptophan on sleepiness and on sleep. Journal of Psychiatric Research. 17:107–13
Hartmann E, Spinweber C L (1979) Sleep induced by 1-tryptophan. Effect of dosages within the normal dietary intake. Journal of Nervous and Mental Disease 167: 497–9
Landry J, Delhaye S (1996) Tryptophan content of foods and feeds. Advances in Experimental Medicine and Biology 398: 703–9
Leathwood P D Fernstrom J D (1990) Effect of an oral tryptophan/carbohydrate load on tryptophan, large neutral amino acid and serotonin and 5-hydroxyindoleacetic acid levels in monkey brain. Journal of Neural Transmission—General Section 79: 25–34
Morin, C. M. (1993a) Appendix F: Sleep diary. In: Insomnia, psychological assessment and management. Guilford Press, New York, pp 209–211
Morin, C. M. (1993b) Appendix B: Sleep impairment index. In: Insomnia, psychological assessment and management. Guilford Press, New York, pp 199–200
Schneider-Helmet D, Spinweber C L (1986) Evaluation of 1-tryptophan for treatment of insomnia: a review. Psychopharmacology 89:1–7

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

What is claimed is:

1. A method of inducing sleep in a human in need thereof, comprising administering to the human a non-toxic, sleep inducing effective amount of a composition comprising at least partially defatted meal from a plant source containing protein-bound tryptophan, and a physiologically acceptable diluent or carrier wherein the plant source is a seed selected from the group consisting of butternut squash seed, peppercorn squash seed, pumpkin seed, lentil seed, sunflower seed, flax seed, watermelon seed, sisymbrium seed, cotton seed, sesame seed, canola seed, evening primrose seed, safflower seed, alfalfa seed, barley, soy bean and combinations thereof.

2. A method of inducing sleep in a human in need thereof, comprising administering to the human a non-toxic, sleep inducing effective amount of a composition comprising at least partially defatted meal from a plant source containing protein-bound tryptophan, and a physiologically acceptable diluent or carrier wherein the plant source is selected from the group consisting of seaweed, kelp and alfalfa seeds.

3. A method of inducing sleep in a human in need thereof, comprising administering to the human a non-toxic, sleep inducing effective amount of a composition comprising at least partially defatted meal from a plant source containing protein-bound tryptophan, and a physiologically acceptable diluent or carrier wherein the composition comprises at least partially defatted butternut squash seed meal having protein-bound tryptophan in an amount of about 25 mg to about 1000 mg tryptophan, from about 25 mg to about 200 mg of glucose and a physiologically acceptable diluent or carrier.

4. A method for providing tryptophan supplementation to a human in need thereof to improve a tryptophan metabolism, comprising administering to a human a non-toxic supplementary effective amount of a composition comprising at least partially defatted meal from a plant source containing protein-bound tryptophan, and a physiologically acceptable diluent or carrier wherein the plant source is a seed selected from the group consisting of butternut squash seed, peppercorn squash seed, pumpkin seed, lentil seed, sunflower seed, flax seed, watermelon seed, sisymbrium seed, cotton seed, sesame seed, canola seed, evening primrose seed, safflower seed, alfalfa seed, barley, soy bean and combinations thereof.

5. A method for providing tryptophan supplementation to a human in need thereof to improve a tryptophan metabolism, comprising administering to a human a non-toxic supplementary effective amount of a composition comprising at least partially defatted meal from a plant source containing protein-bound tryptophan, and a physiologically acceptable diluent or carrier wherein the plant source is selected from the group consisting of seaweed, kelp and alfalfa seeds.

6. A method for providing tryptophan supplementation to a human in need thereof to improve a tryptophan metabolism, comprising administering to a human a non-toxic supplementary effective amount of a composition comprising at least partially defatted meal from a plant source containing protein-bound tryptophan, and a physiologically acceptable diluent or carrier wherein the composition comprises at least partially defatted butternut squash seed meal having protein-bound tryptophan in an amount of about 25 mg to about 1000 mg tryptophan, from about 25 mg to about 200 mg of glucose and a physiologically acceptable diluent or carrier.

7. A method as defined in claim 1, 2, 3, 4, 5, or 6 wherein the human suffers from insomnia.

8. The method of claim 1, 2, 3, 4, 5, or 6 wherein the composition further comprises a carbohydrate source having a high glycemic index.

9. The method of claim 8 wherein the carbohydrate source is selected from the group consisting of glucose, maltose, sucrose and combinations thereof.

10. The method of claim 1, 2, 3, 4, 5, or 6 wherein the composition further comprises a vitamin selected from the group consisting of vitamin B3, B6 and combinations thereof in an amount sufficient to enhance uptake of the tryptophan across the blood/brain barrier.

11. The method of claim 1, 2, 3, 4, 5, or 6 wherein the composition is in the form of a tablet, powder, suspension, liquid, capsule or gel.

12. The method of claim 1, 2, 3, 4, 5, or 6 wherein the composition is in the form of a dietary supplement.

13. The method of claim 1, 2, 3, 4, 5, or 6 wherein the composition further comprises from about 5 mg to about 50 mg vitamin B3; from about 0.5 mg to about 50 mg vitamin B6, and combinations thereof.

14. The method of claim 3 or 6 wherein the composition comprises at least partially defatted butternut squash seed meal providing from about 25 mg to about 50 mg tryptophan, from about 75 mg to about 100 mg of glucose and a physiologically acceptable diluent or carrier.

* * * * *